(12) United States Patent
Baker et al.

(10) Patent No.: US 7,312,250 B2
(45) Date of Patent: Dec. 25, 2007

(54) FLUORINE-SUBSTITUTED ALKYL PHENOL COMPOUNDS AND THEIR USES

(75) Inventors: Max T. Baker, Iowa City, IA (US); Mohamed Naguib, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 10/095,810

(22) Filed: Mar. 12, 2002

(65) Prior Publication Data

US 2003/0176513 A1 Sep. 18, 2003

(51) Int. Cl.
*A61K 31/05* (2006.01)
*C07C 39/24* (2006.01)
(52) U.S. Cl. ............... 514/731; 514/737; 568/775
(58) Field of Classification Search ............... 568/775, 568/700, 731; 514/731
See application file for complete search history.

(56) References Cited

U.S. PATENT DOCUMENTS

| | | | | |
|---|---|---|---|---|
| 3,346,668 | A | * | 10/1967 | Dalton |
| 3,899,517 | A | * | 8/1975 | Flectcher |
| 3,979,463 | A | * | 9/1976 | Endres |
| 4,044,153 | A | * | 8/1977 | Schultz |
| 4,067,996 | A | * | 1/1978 | Najer |
| 4,731,450 | A | * | 3/1988 | Wakselman |
| 4,982,006 | A | * | 1/1991 | Hudec |
| 5,308,874 | A | | 5/1994 | Sanchez et al. ............ 514/731 |
| 5,461,080 | A | | 10/1995 | Sanchez et al. ............ 514/731 |
| 5,496,537 | A | | 3/1996 | Henry ..................... 424/45 |
| 6,254,853 | B1 | | 7/2001 | Hendler et al. ............ 424/45 |
| 2001/0004664 | A1 | | 6/2001 | Asami et al. ............. 528/141 |

FOREIGN PATENT DOCUMENTS

JP 04-285672 10/1992
JP 4-285672 * 10/1992

OTHER PUBLICATIONS

Krusz, et al.; "Intravenous Propofol: Unique Effectiveness in Treating Intractable Migraine"; *Headache*; (2000), 40: 224-230.
Aarts, et al.; "The widely used anesthetic agent propofol can replace α-tocopherol as an antioxidant"; *FEBS Let.*; (1995), 357(1): 83-85.
Borgeat, et al.; "Propofol and Cholestatic Pruritus"; *Amer. Journ. of Gastroent.*; (1992), 87(5): 672-674.
Sagara, et al.; "Propofol Hemisuccinate Protects Neuronal Cells from Oxidative Injury"; *J. Neurochem.*; (1999), 73(6): 2524-30.
Jevtovic-Todorovic, et al.; "Propofol and sodium thiopental protect against MK-801-induced neuronal necrosis in the posterior cingulate/retrosplenial cortex"; *Brain Res.*; (2001), 913(2): 185-9.
Kelly, et al.; "Propofol in the treatment of moderate and severe head injury: a randomized, prospective double-blinded pilot trial"; *Journ. of Neurosurg.*, (1999), 90: 1042-1052.
Briggs, et al.; "An adverse reaction to the administration of disoprofol (Diprivan)"; *Anethesis*; (1982), 37: 1099-1101.
McHugh, et al.; "Propofol emulsion and bacterial contamination"; *Can. J. Anaesth.*; (1995), 42(9): 801-804.
International Search Report based on PCT/US03/07146 dated Jun. 30, 2003.

* cited by examiner

*Primary Examiner*—Rosalynd Keys
(74) *Attorney, Agent, or Firm*—Edwards Angell Palmer & Dodge LLP; Kathleen M. Williams; Mark D. Russett

(57) ABSTRACT

The present invention relates to the synthesis of fluorinated forms of alkyl phenol compounds and their subsequent use as pharmaceutical agents. More specifically, alkyl phenol compounds are fluorinated to increase compound volatility such that the compound may be administered to a mammal, such as a human being, by inhalation. The invention also provides an inhaler (or vaporizer), that can be used for administration of the volatile derivatives of fluorine-substituted alkyl phenol compound. Further, different derivatives of fluorine-substituted alkyl phenol compound can be also administered by other routes as described in this document.

10 Claims, 1 Drawing Sheet

US 7,312,250 B2

FLUORINE-SUBSTITUTED ALKYL PHENOL COMPOUNDS AND THEIR USES

FIELD OF THE INVENTION

The invention relates to the synthesis of fluorine-substituted alkyl phenol compounds and their use as medicinal agents.

BACKGROUND OF THE INVENTION

Alkyl phenols have a broad range of medicinal properties ranging from central nervous system (CNS) effects to antioxidant activities. The effects of alkyl phenols on the CNS are generally sedative in nature. For example, the dialkylphenol, propofol (2,6-diisopropylphenol is used as anesthetic agent in both humans and animals. This compound also serves as a muscle relaxant, anti-epileptic, anti-emetic, anti-spasmotic and as a bronchodilator. Importantly, recent studies demonstrate that administration of propofol to subjects leads to cessation of migraines (Kruse et al., 2000, *Headache* 40: 224-230).

Diisopropylphenol also has uses in the treatment of pathologies relating to the presence of free oxygen radicals (see, see, e.g., U.S. Pat. No. 5,308,874; U.S. Pat. No. 5,461,080; and Aarts et al., 1995, *FEBS Let.* 357(1): 83-5). For example, propofol has been used to inhibit inflammatory responses of the upper respiratory tract due to oxidative stress (see, e.g., Zaloga et al., The Internet Journal of Emergency and Intensive Care Medicine™ $^{ISSN}$ 1092-4051; Borgeat et al., 1992, *American J. of Gastroent.* 87(5): 672-674). Propofol also has been shown to repair neural damage caused by free oxygen radicals in vitro (Sagara et al., 1999, *J Neurochem.* 73(6): 2524-30; Jevtovic-Todorovic et al., 2001, *Brain Res.* 913(2): 185-9) and has been used in vivo to treat head injury (see, e.g., Kelly et al., *Journal of Neurosurgery* 90: 1042-1052, 1999).

The only recognized method for delivery of alkylphenols is by intravenous (iv) injection in a lipid-based emulsion. After iv administration, propofol is rapidly distributed from the blood into highly perfused areas such as heart, lung, and liver. Propofol also is rapidly distributed to tissues because of its high solubility in lipids. This high solubility enables propofol to cross the blood-brain barrier easily. However, the oil emulsion forms of propofol contain a high concentration of lipids that potentiate hyperlipidemia, and frequently cause pain upon injection (see, e.g., Lowrey et al., 1996, *Nutr Clin Pract.* 11: 147-149; Kress et al., *Am. J. Respir. Crit. Care Med.* 153: 1012-1018; Cerra et al., 1997, *Chest.* 111: 769-777).

An inhalant form of an alkylphenol is desirable as a pre-anesthetic or anesthetic agent because no iv injection is required. In addition, an inhalable form of an alkyl phenol is desirable for treatment of respiratory disorders and migraines, where rapid action is desired. However, delivery of alkylphenols by inhalation has been problematic because alkyl phenols generally are not sufficiently volatile at low temperature. Therefore, inhalable forms of propofol must be heated or delivered in formulations in which they are soluble and can be aerosolized. For example, aerosols comprising lipid-based microdroplets of propofol have been reported (see, e.g., U.S. Patent Application No. 20010004644) as well as formulations comprising propofol dissolved in tetrafluoroethane (see, e.g., U.S. Pat. No. 5,496,537). However, formulations that contain emulsifiers or solubilizers cause problems such as allergic complications (see, e.g., Briggs et al., *Anesthesis* 37: 1099) and contamination (McHugh et al., 1995, *Can J. Anaesth.* 42(9): 801-804). Water soluble pro-drug forms of propofol esters have been described (see, e.g., U.S. Pat. No. 6,254,853); however, these compounds generally are administered as aerosols in the presence of both a surfactant and a propellant and must be metabolized first in the body to a bioactive form. Further, it would be unlikely that propofol pro-drugs would provide sufficient propofol blood concentrations to induce general anesthesia in surgical patients.

SUMMARY OF THE INVENTION

The present invention relates to the synthesis of fluorinated forms of alkyl phenol compounds and their subsequent use as pharmaceutical agents. More specifically, alkyl phenol compounds are fluorinated so that there is an increase compound volatility such that the compound may be administered to a mammal, such as a human being, by inhalation. The invention also provides an inhaler (or vaporizer), which provides an inhalable form of fluoroalkylphenol. In addition to inhalation, the novel fluoroalkylphenol compounds may be administered by intravenous, transdermal, intranasal, transmucosal, vaginal and rectal routes, so that compounds are provided that can be administered by multiple routes including inhalation.

In one aspect, the method provides a composition comprising a fluorine-substituted alkyl phenol compound. Preferably, the alkyl phenol compound is not an ester and has at least two fluorine substituents. Fluorine can be substituted for any hydrogen at a carbon-hydrogen bond in the alkyl phenol compound; however, preferably, fluorine is provided on the alkyl side groups at the 2- and 6- positions of phenol. In another aspect, the composition comprises an alkyl phenol and one or more fluorine substitutions at any one or more of the two meta and one para positions of the aromatic ring of the alkyl phenol.

In one aspect, the alkyl group of the compound is sec-butyl. In another aspect, the alkyl group is isopropyl. In another aspect the alkyl group is methyl. In one aspect, the alkyl phenol is a dialkylphenol. In another aspect, the alkyl phenol is a diisopropylphenol. In still another aspect, the alkyl phenol is a di-sec-butylphenol. In a further aspect, the alkyl phenol is 2,6-diisopropylphenol. In still a further aspect, the alkyl phenol is 2,6-di-sec-butylphenol. In another aspect, the alkylphenol is 2-isopropyl, 6-methyl phenol. In another aspect, the alkylphenol is 2-sec-butyl, 6-methyl phenol In one aspect, the invention provides a pharmaceutical composition comprising any of (but not limited to) the compositions described above and a pharmaceutical carrier.

The invention further provides a method for anesthetizing a subject comprising administering to subject a pharmaceutically effective amount of the pharmaceutical composition described above. In one aspect, the pharmaceutically effective amount is an amount sufficient to achieve a sedation level of at least 2 on the Ramsay scale. In another aspect, the pharmaceutically effective amount is an amount sufficient to achieve a sedation level of at least 3 on the Ramsay scale. In still another aspect, the pharmaceutically effective amount is an amount sufficient to achieve a sedation level of at least 4. In a further aspect, the pharmaceutically effective amount is an amount sufficient to achieve a sedation level of at least 5 on the Ramsay scale.

The invention also provides a method for treating a tissue comprising an excess of free oxygen radicals comprising exposing said tissue to an amount of a pharmaceutical composition as described above, effective to reduce the amount of free radicals in the tissue compared to tissue not so treated (e.g., by at least 10%). In one aspect, the tissue is in a patient with a pathology associated with an excess of free oxygen radicals. In one aspect, the pathology is an inflammatory disease. In another aspect, the pathology is a neurological disease. In still another aspect, the pathology is cancer. In a further aspect, the pathology is a cerebrovascular disease. The method preferably comprises the step of administering the composition by inhalation.

The invention also provides a method of treating a headache, which comprises administering a therapeutically effective amount of a pharmaceutical composition as described above to a patient. In one aspect, the headache is a migraine. In another aspect, the therapeutically effective amount is an amount effective to reduce one or more symptoms of: pain, visual disturbance, auditory disturbance, and nausea.

The invention further provides an inhaler (or vaporizer) for delivering a pharmaceutically effective amount of the composition as described above, wherein the inhaler comprises: a reservoir comprising a fluorine-substituted alkyl phenol; an opening for placement in the oral or nasal cavity of a patient, and a passageway connecting said reservoir and said opening, wherein a vapor form of said fluorine-substituted alkyl phenol passes through said passageway from said reservoir through said opening into the oral or nasal cavity of said patient for inhalation by said patient.

The invention features a process for preparation of a compound of the formula:

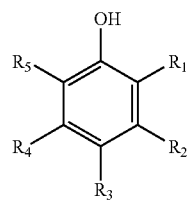

where $R_1$ is a $C_1$ to $C_6$ linear or branched alkyl, $C_1$ to $C_6$ linear or branched fluoroalkyl containing at least one fluorine atom provided that when $R_1$ and $R_5$ are both alkyl, R1 is not equal to $R_5$. The process of preparation of this compound comprises the steps of:
i) reacting an alkyl phenol of the formula:

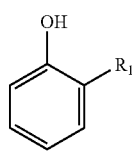

with a halogenation agent to give a haloalkyl phenol of the formula:

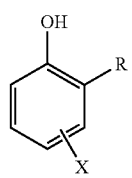

where $R_1$ is a $C_1$ to $C_6$ linear or branched alkyl, $C_1$ to $C_6$ linear or branched fluoroalkyl containing at least one fluorine atom provided that when $R_1$ and $R_5$ are both alkyl, $R_1$ is not equal to $R_5$ where X═Cl, Br or I
ii) reacting the haloalkyl phenol with a fluoroalkylating agent to give a fluoroalkyl phenol of the formula:

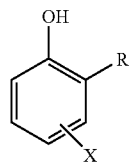

where $Ry = \begin{array}{c} Ra \\ | \\ -C-Rb; \\ | \\ Rc \end{array}$ and where $R_a$, $R_b$ and $R_c$ are each independently H, F, straight or branched alkyl chain containing at least one F atom.

In a preferred embodiment, $R_1$ is selected from the group consisting of $CH_3$ (methyl), $CH_2CH_3$ (ethyl), $CH(CH_3)_2$ (isopropyl), $CH_2CH_2CH_3$ (n-propyl), or $CH(CH_3)CH_2CH_3$ (sec-butyl), $CF_3$ (trifluoromethyl), $CF_2CF_3$ (pentafluoroethyl), $CF_2CF_2CF_3$ (septafluoro-n-propyl), $R_2$ and $R_4$ are H (hydrogen) and $R_3$ and $R_5$ are independently selected from H, $CF_3$, $CF_2CF_3$ or $CF_2CF_2CF_3$.

In a preferred embodiment the fluoralkyl is selected from the group consisting of 6-trifluoromethyl-2-sec-butylphenol, 6-trifluoromethyl-2-isopropylphenol, 6-Pentafluoroethyl-2-isopropylphenol, and 6-Heptafluoro-n-propyl-2-isopropylphenol.

In a preferred embodiment, the halogenating agent is a bromination or iodination agent.

In a preferred embodiment, the halogenating agent is selected from the group consisting essentially of $Br_2$ and CuI.

In a preferred embodiment, the halogenating agent is CuI.

In another preferred embodiment, the fluoroalkylating agent is selected from the group consisting essentially of methyl 2,2-difluoro-2-(fluorosulfonyl)acetate, sodium heptafluorobutyrate and $CF_3CF_2COONa$ (perfluoro sodium propionate).

In another preferred embodiment, the fluoroalkylating agent is methyl 2,2-difluoro-2-(fluorosulfonyl)acetate.

In another preferred embodiment, the fluoroalkylating agent is perfluoro sodium proplonate.

In one aspect of the invention, the synthesis includes substituting at least one hydrogen atom in the aromatic ring of the fluoroalkyl phenol with a fluorine atom.

In another aspect of the invention, $R_1$ and said $R_5$ of the synthesized alkyl phenol are both alkyl groups provided that the $R_1$ is different from $R_5$.

In another aspect of the invention, $R_1$ and said $R_5$ of the synthesized alkyl phenol are interchangeably alkyl and fluoroalkyl.

BRIEF DESCRIPTION OF THE FIGURES

The objects and features of the invention can be better understood with reference to the following detailed description and accompanying drawings.

DETAILED DESCRIPTION

Figure 1:
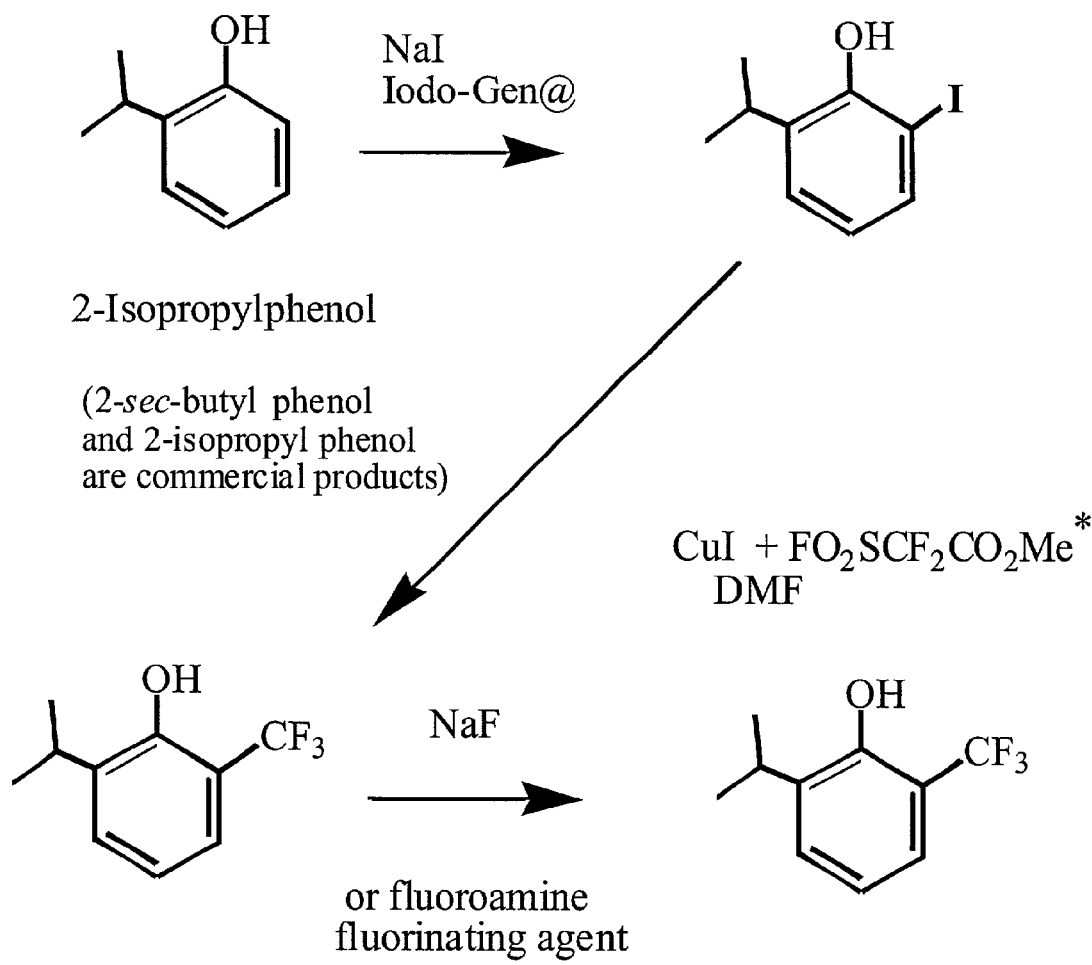
FIG. 1 shows a schematic of an exemplary synthesis scheme according to one aspect of the invention.

The present invention describes the formulation of novel fluorine-substituted alkyl phenols that can be delivered by inhalation, or any other routes (eg, intravenous, intramuscular, orally, rectally, vaginal, sublingual, transcutaneous with or without the use of solvents or emulsifiers.

Definitions

The objects and features of the invention can be better understood with reference to the following detailed description and accompanying drawings.

As used herein, "volatile" refers to a compound, at least 10% of which exists in a vapor form at room temperature (e.g., from 15° C.-42° C.). Volatility can be measured as a function of mass change of the compound as a function of temperature using a standard thermogravimetric analyzer (e.g., model DT-40, available from Shimadzu Corporation, Japan).

As used herein, "R groups independently selected" indicates that two or more of the groups may be identical or each R group may be different.

As used herein, "alkyl" refers to saturated hydrocarbon groups that can be either straight-chain or branched-chain.

As used herein, "alkoxy" refers to alkyl radicals that are attached to the phenolic ring through the oxygen (e.g., a methoxy group). The term "heteroatom" is used herein to refer to oxygen, sulfur and nitrogen atoms. This is not relevant to include because we are not patenting compounds modified on the hydroxyl group.

As used herein, "pharmaceutically acceptable carrier" or "therapeutically acceptable carrier" means any substance that when combined with the compounds described herein does not interfere with the effectiveness or the biological activity of the active ingredients of the compound and which is not toxic to the hosts, which may be either humans or animals, to which it is administered.

As used herein, a "therapeutically effective amount" refers to the amount of compound sufficient to induce a desired biological result. A "desired biological result" may be alleviation of the signs, symptoms, or causes of a disease, or any other desired alteration of a biological system.

As used herein, "subject" refers to any mammal to which the compositions of the invention may be administered. Subjects specifically intended for treatment with the compositions and methodologies of the present invention include humans, as well as non-human primates, sheep, horses, cattle, goats, pigs, dogs, cats, rabbits, guinea pigs, poultry, hamsters, rats and mice, as well as the organs, tumors and cells derived or originating from these hosts.

As used herein, "a pathological condition" means a disease or trauma that causes structural and functional changes in tissues and organs. Thus, as defined herein, a "pathological condition" encompasses both diseases and abnormal physiological responses. For example, a stroke or an immune response that might occur after an organ transplant would be encompassed by the term "pathological condition."

As used herein, "CNS properties" of alkyl phenols means any pharmacological mechanism of action that has an effect on the central nervous system of a mammal.

As used herein, "dysfunction of the CNS" means any change in central nervous system activity that is detrimental to the subject.

As used herein, "detrimental" means painful, uncomfortable, harmful, debilitating or disfiguring for the subject. CNS disorders include, for example, migraine, cluster headaches, neurodegenerative diseases and others.

As used herein, a nerve is "anesthetized" when the ability of the nerve to generate or conduct impulses is significantly impaired, relative to the capacity of the nerve structure to generate or conduct nerve impulses in the absence of exposure to an anesthetic agent (e.g., a fluorine-substituted alkyl phenol).

As used herein, "a passageway connecting" refers to a passageway which is open at a first and second end, the first end connecting, either directly or indirectly with the opening of a reservoir in an inhaler (or vaporizer) device, the second end connecting, either directly or indirectly with an opening in inhaler device.

As used herein, an "excess of free radicals" refers to an amount of free radicals that are detrimental to biological systems. Detrimental can mean a causing a disease state that is believed to be caused by or exacerbated by processes involving free radicals.

As used herein, "halogenating agent" refers to a compound that incorporates a halogen onto the benzene ring. Halogens are the non-metallic elements in group VII of the periodic table (i.e. fluorine, chlorine, bromine, iodine and astatine). A preferred halogenating agent according to the invention is CuI.

As used herein, "fluoroalkylating agent" refers to a compound that incorporates a fluorine atom onto an alkyl group. Preferred fluoroalkylating agents according to the invention are methyl 2,2-difluoro-2-(fluorosulfonyl)acetate, sodium heptafluorobutyrate and $CF_3CF_2COONa$ (perfluoro sodium propionate).

As used herein, "fluoroalkyl" refers to $C_1$ to $C_6$ straight or branched alkyl chains containing at least one fluorine atom.

Fluorine-Substituted Alkyl Phenols

Preferred fluorine-substituted alkyl phenol compounds according to the invention have the following structural formula:

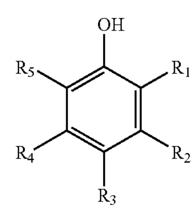

We claim the compounds of the structure above where:

$R_1$ is independently selected from $CH_3$ (methyl), $CH_2CH_3$ (ethyl), $CH(CH_3)_2$ (isopropyl), $CH_2CH_2CH_3$ (n-propyl), or $CH(CH_3)CH_2CH_3$ (sec-butyl), $CF_3$ (trifluoromethyl), $CF_2CF_3$ (pentafluoroethyl), $CF_2CF_2CF_3$ (septafluoro-n-propyl)

$$R_2=R_3=R_4=H$$

$R_5$ is independently selected from $CF_3$, $CF_2CF_3$, $CF_2CF_2CF_3$

We claim compounds of the structure above where:

$R_1$ is independently selected from $CH_3$ (methyl), $CH_2CH_3$ (ethyl), $CH(CH_3)_2$ (isopropyl), $CH_2CH_2CH_3$ (n-propyl), or $CH(CH_3)CH_2CH_3$ (sec-butyl), $CF_3$ (trifluoromethyl), $CF_2CF_3$ (pentafluoroethyl), $CF_2CF_2CF_3$ (septafluoro-n-propyl)

$$R_2=R_3=R_5=H$$

$R_4$ is independently selected from $CF_3$, $CF_2CF_3$, $CF_2CF_2CF_3$

We also claim compounds of the structure above where:

$R_1$ is independently selected from $CH_3$ (methyl), $CH_2CH_3$ (ethyl), $CH(CH_3)_2$ (isopropyl), $CH_2CH_2CH_3$ (n-propyl), or $CH(CH_3)CH_2CH_3$ (sec-butyl), $CF_3$ (trifluoromethyl), $CF_2CF_3$ (pentafluoroethyl), $CF_2CF_2CF_3$ (septafluoro-n-propyl)

$R_2=R_4=R_5=H$ $R_3$ is independently selected from $CF_3$, $CF_2CF_3$, $CF_2CF_2CF_3$.

In the above formula, $R_1$ and $R_5$ are independently selected and may also comprise functional groups including, but not limited to, hydrogen (H) and lower alkyls of 1 to 6, and preferably, 1-4 carbon atoms. In one aspect, $R_1$ and $R_5$ are independently selected from the group consisting of H, —$CH(CH_3)_2$, [isopropyl] or —$C(CH_3)CH_2CH_3$ [sec-butyl] $R_2$, $R_3$ and $R_4$ are independently selected and may be functional groups including, but not limited to H and F (fluorine).

In one aspect, $R_1$ and $R_5$ is selected from the group consisting of —$CH_3$, —$CH(CH_3)_2$, or —$C(CH_3)CH_2CH_3$. More preferably, the compound comprises at least two fluorine substituents. In one aspect, the akyl phenol has one or more fluorine substitutions at any of the two meta (positions 3 and 5) and single para position 4) positions of the alkyl phenol's aromatic ring. More preferrably the methyl group is substituted with three fluorines. A desired compound is the methyl group substituted with three fluorines and the aromatic positions (positions 3-5) substituted with one, two or three fluorines.

Exemplary compounds include a fluorine-substituted 2,6-diisopropyl phenol; a fluorine-substituted 2-methyl-6-isopropylphenol; a 2,6 di-sec-butylphenol, a 2-methyl-6-sec-butylphenol. As used herein, "a fluorine-substituted" compound comprises at least one fluorine group, and preferably, at least two fluorine groups replacing a hydrogen at a carbon-hydrogen bond within the compound. Specifically preferred compounds according to the invention is a fluorine-substituted 2,6-diisopropylphenol and a fluorine-substituted 2-methyl-6-isopropylphenol. Preferably, compounds according to the invention are not esters.

In a most preferred embodiment of the above formula, R1 is an alkyl and R5 is a fluoroalkyl.

In all instances, R1 and R5 of the above formula are not identical.

Fluoroalkylphenol Synthesis

6-Iodo-2-isopropylphenol and 6-iodo-2-sec-butylphenol were synthesized according to the method of Vakkuri et al (1984) ((Vakkuri O, Leppalouto J, Vuolteenaho, O. Acta Endocrinologica, 106:152-157, 1984; see FIG. 1). The iodoalkylphenols were separated by distillation and each isomer was identified by proton NMR. The starting iodoalkylphenol was then dissolved in dimethylformamide (DMF) in a glass flask fitted with a condenser. CuI and methyl 2,2-difluoro-2-(fluorosulfonyl)acetate were added and the reaction mixture heated to 60-80° C. for at least 3 hr. The displacement of iodine on melatonin was expected to proceed according to the mechanisms described by Burton D J, Yang Z-Y (1992) Tetrahedron 48:189-275.

Following the reaction period, the reaction mixture was chilled on ice and DMF removed from the mixture by rotatory evaporation. Water was added and the reaction mixture neutralized. Melatonin products are extracted from the aqueous with methylene chloride. The products of the reaction were directly analyzed by GC/MS at this stage.

Product purification was performed by vacuum distillation. Proton and Fluorine NMR confirmed the identity of the products.

Additional schemes for the synthesis of the fluorinated alkylphenols of the present invention are described in the Examples.

Pharmaceutically Acceptable Carriers

Some of the fluorine-substituted alkyl phenols of this invention that are volatile at room temperature can be delivered alone to the respiratory tract as an inhalant. Additional compounds of less volatility (e.g., accessory therapeutic agents) may be delivered by other routes (e.g., intravenous, intramuscular, orally, rectally, vaginally, transmucosal, transcutaneous) along with a pharmaceutically acceptable carrier. The carrier can be any standard buffer, for example, phosphate buffered saline, a sugar solution, such as dextrose solution, or an emulsion, such as oil/water or water/oil emulsion. Pharmaceutically acceptable formulations are described in Remington's Pharmaceutical Sciences (Mack Pub. Co., N.J. 1995). Liposomes are included within the definition of a pharmaceutically acceptable carrier.

Methods of Delivery

The fluorine-substituted alkyl phenol compounds described above can be delivered by any route of administration that is known in the art. Some of the compounds are particularly suited for methods of delivery by inhalation because they are volatile at room temperature. The method for delivery of the compounds also can be parenteral, enteral, and/or transdermal. For example, administration can be oral, vaginal, rectal, or sublingual or by injection (e.g., intravenous, subcutaneous, and intramuscular).

Delivery to The Respiratory Tract

The volatile fluorine-substituted alkyl phenols of the invention are preferably delivered to the respiratory tract as a vapor inhalant.

In another aspect, various forms of biological tissue are placed in environmental chambers, tents or enclosures that contain effective amounts of fluorine-substituted alkyl phenols according to the invention. In one aspect, a subject, such as a human being, is placed within the chamber and exposed to a fluorine-substituted alkyl phenol according to the invention.

In preferred aspect, a fluorine-substituted alkyl phenol is one element of a gas mixture delivered with a breathing device (e.g., a respirator or lung machine). Fluorine-substituted alkyl phenol compounds also can be added to a vaporizer (i.e., a device used to vaporize medicines and other compounds) and upon vaporization, can be inhaled into the respiratory tract of a subject to achieve a therapeutic effect. Additionally, fluorine-substituted alkyl phenol compounds can be added to a hand-held inhaler (i.e., a device that produces a vapor to medicate by inspiration) and upon inhalation, the compounds can be delivered to the lungs, i.e., via the nasal passageways or via the mouth. Preferably, the inhaler device is hand-held and designed for self-administration without the aid of medical personnel.

In one aspect, an inhaler for delivering compounds according to the invention comprises a reservoir of a fluorine-substituted alkyl phenol and a passageway connecting with a chamber having an opening for placement in the oral or nasal cavity of a patient. When air passes over the fluorine-substituted alkyl phenol through the passageway, vapors are inhaled. The reservoir can contain a liquid form of a fluorine-substituted alkyl phenol or an absorbable material comprising a fluorine-substituted alkyl phenol. In one aspect, the chamber is configured to fit within the mouth or nasal cavity of a patient.

The inhaler further can comprise a mechanism for enhancing the rate of vaporization of materials in the reservoir, e.g., such as means for introducing a gaseous medium, such as compressed air, under pressure into the reservoir, for example, through the use of a small electrical pump or a manually operated bulb. Other means for enhancing the vaporization of a volatile liquid in an inhaler are described in U.S. Pat. No. 4,566,451, for example, the entirety of which is incorporated by reference herein.

Preferably, total dosage in this type of device would be sub-anesthetic and sub-lethal. For example, doses from 0.1% to 70% can be delivered where sub-anesthetic doses are desired, while larger doses from can be delivered (e.g., over a period of from about one to 15 minutes) where anesthetic effects are desired. In a preferred embodiment, does from between 0.1-10% are delivered. The inhaler device further can contain an odor modifying or masking agent, a taste-masking or modifying agent, and/or an irritant inhibiting or preventing agent. Alternatively, these agents can be administered separately. Some examples of suitable inhaler devices can be found in U.S. Pat. No. 6,234,169 and U.S. Pat. No. 6,190,691, the entireties of which are incorporated by reference herein.

Alternatively, a fluorine-substituted alkyl phenol compound is added to a filter or some other delivery reservoir in an inhaler device such that as air is drawn through the device, the compound is vaporized and subsequently inhaled. When the vapor form of the fluorine-substituted alkyl phenol is inhaled through the use of the inhaler device, the compound is brought into the respiratory tract of a subject using the device.

Delivery by Injection

Compounds described herein may be injected subcutaneously, intravenously or intramuscularly. Pharmaceutically acceptable carriers suitable for injections are aqueous and can include bactericidal agents or stabilizers. Further, intravenous solutions may include detergents and emulsifiers such as lipids (although the latter are not preferred). The concentration of compound in an aqueous solution can range from 1 mg/ml to 100 mg/ml.

Oral or Transdermal Delivery

Pharmaceutical compositions that include pills, tablets, powders or capsules comprising a fluorine-substituted alkyl phenol can be delivered orally. Typically, the composition contains 10%-95% active ingredient. Some examples of nontoxic solid carriers include mannitol, lactose, starch, magnesium stearate, magnesium carbonate, sodium saccharine, propylene glycol, talcum, rice, flour, chalk, dried skim milk and sugars, such as cellulose, fructose, glucose, maltose, or sucrose. Other carriers include, oils, such as vegetable oil or synthetic oil, and suitable excipients include lactose, sucrose, gelatin, maltose, and others. A unit dose in a tablet form can range from about 10 mg to 2 g of compound.

Therapeutic Uses of Fluorine-Substituted Alkyl Phenols

When a compound according to this invention is administered to a human subject, the daily dosage of the compound normally will be determined by the prescribing physician with the dosage generally varying according to the age, weight, and response of the individual patient, as well as the severity of the patient's symptoms. Dosage may be optimized performing any of the assays described below for particular treatment regimens.

Treatment of Migraines

The fluorine-substituted akyl phenols of this invention are particularly useful for treatment of migraine headaches. Migraine is a disorder characterized by a persistent headache that may be associated with visual disturbances, nausea, and vomiting. Severe head pain can also be caused by muscle tension in the head and neck area. The headache can be accompanied by intracranial inflammation, extracranial inflammation, and/or cerebral inflammation. People who experience migraines may have an episode daily, monthly, or only once a year. An untreated migraine episode can persist for hours or even days. Migraines can be recurrent and in some cases, visual changes (e.g., auras) or other symptoms precede the onset of a migraine.

The precise cause of a migraine is unknown; however, alterations in cerebral blood flow are known to be involved (e.g. Berkow et al., ed., 1992, The Merck Manual of Diagnosis and Therapy, Merck Research Laboratories, Rahway, N.J., pp. 1425-1426). It is hypothesized that migraines result from release of neurotransmitters by trigeminal nerves. The trigeminal nerves innervate cerebral blood vessels (Moskowitz et al., 1979, *Lancet* 2: 883-885) and inflammation occurs upon neurotransmitter release (Demarin et al., 1994,*Funct. Neurol.* 9:235-245; Moskowitz, 1984, *Ann. Neurol.* 16:157-168; Moskowitz, 1993, *Neurol.* 43(Suppl. 3): S16-S20). Although the mechanism of action of akyl phenols is not fully understood, propofol is known to be an agonist of gamma aminobutyric acid A ($GABA_A$) receptors. The compound's agonist activity leads to inhibition of neuronal firing which in turn contributes to its anesthetic properties.

The fluorine-substituted alkyl phenols of this invention may be delivered to subjects by any established method of administration, including, but not limited to oral, transdermal, intravenous, and delivery to the respiratory tract. However, the volatile fluorinated alkyl phenols described herein allow for easy administration by an inhaler device, permitting fast, effective delivery of the drug. The pharmaceutically effective dose for the reduction of headache ranges from about 50 mg to 200 mg of compound. Preferably, the compounds are used to treat any of: migraine, an individual headache episode, a cluster headache, a headache associated with vascular disease, a tinnitus episode, a neurovascular disorder associated with cephalic inflammation.

Efficacy of treatment using particular compounds can be optimized using a headache rating system, e.g., such as the four-point rating system used by the International Headache Society (HIS) (*Cephalagia* 8(*Suppl.* 7): 19-28) or the ten-point system described in U.S. Patent Application No.20010004644. For example, five minutes after completion of administration of a fluorine-substituted alkyl phenol according to the invention, a patient can be asked to rate perceived headache pain. If no pain relief is obtained, administration can be repeated until a peak is achieved, for up to about 90 minutes. Preferably, an effective dose is one which results in at least 50% reduction in the severity of migraine symptoms, e.g., one or more of pain, visual disturbances (e.g., photophobia), aural disturbances (e.g., ringing, whistling sounds, tinnitus, and the like), and nausea.

Use as a Sedative and Anesthetic Agent

The compounds according to the invention are preferably used as therapeutic agents with effects on the central nervous system including sedation and anesthesia.

Sedatives are commonly used to reduce or eliminate symptoms of agitation and restlessness that accompany anxiety. Anxiety is a sustained state of apprehension in response to a real or perceived threat and is associated with motor tension and increased sympathetic activity (Crippen et al., 1992, *Crit Care Nurs Q.* 15: 52-74). Adverse effects of agitation include increases in respiratory rate, heart rate, blood pressure, cardiac contractility, afterload, dysrhythmias, and myocardial oxygen consumption (Crippen, 1992, supra; Harvey, 1996, *Am J Crit Care.* 5: 7-18). Use of sedation can prevent physical injury, and can be used in critical care to decrease the activity of a patient, for example, to decrease myocardial oxygen consumption.

Short-term sedation (from several hours to 5 days) may be necessary to reduce anxiety and agitated movements that can affect hemodynamic stability. The fluorine-substituted alkyl phenols of the present invention can be used to reduce or eliminate anxiety during painful or uncomfortable procedures, reduce restlessness in the initial hours after surgery, decrease agitation in patients with neurological disorders or injury; and promote synchronous breathing in patients receiving mechanical ventilation (Roekaerts et al., 1993, *J Cardiothorac Vasc Anesth.* 7: 142-147).

When a fluorine-substituted alkyl phenol is used as a sedative, the dose should be titrated to attain the desired level of sedation. Optimal dosage also may be determined by assessing the level of sedation of a patient at a give dose. For example, the Ramsay scale can be used, in which a sedation level of 1 corresponds to a patient who is anxious, agitated and/or restless; a sedation level 2 corresponds to a patient who is cooperative, accepting ventilation, oriented, and tranquil; a sedation level 3 corresponds to a sleeping patient who exhibits a brisk response to a light glabeller tap or a loud auditory stimulus; a sedation level of 4 corresponds to a sleeping patient who only sluggishly responds to a light glabellar tap or loud auditory stimulus, but who does respond to a painful stimulus; and a sedation level of 5 corresponds to a sleeping patient who does not respond to even a painful stimulus (see, e.g., Ramsay et al., 1974, *BMJ.* 2: 656-659). Use of the scale requires hourly assessment of sedation at levels 3 and 4. Neurological assessment should be performed at least every 24 hours.

Because of the rapid onset of action of alkyl phenols and the rapid decrease in blood concentrations after cessation of delivery, neurological assessment does not require prolonged cessation of sedation. For example, the dose can be decreased or stopped to decrease the level of sedation and the patient's level of consciousness can be evaluated. The amount of sedation used generally will depend on the patient's condition. During daytime hours, sedation might be kept at levels 2 to 3 on the Ramsay scale to accommodate a sleep-wake cycle. Greater sedation, for example, levels 4 or 5, might be used at night or during painful procedures.

Preferably, subjects treated with fluorine-substituted alkyl phenols are able to awaken within 10 to 20 minutes after cessation of delivery. Rapid awakening or abrupt withdrawal of compounds may cause increased anxiety, agitation, and resistance to mechanical ventilation (see, e.g., Mirenda and Broyles, 1995, *Chest* 108: 539-548). These effects can be reduced or prevented by decreasing dosage in small increments (5 µg/kg per minute) during a period of about 5 to 10 minutes.

Preferably, compounds according to the invention are used for short-term sedation. However, in one aspect, the compounds are administered for longer periods over several days, for example, in the case of severe respiratory failure or status epilepticus (see, e.g., Ronan et al., 1995, *Crit. Care Med.* 23: 286-293; Carrasco et al., 1993, *Chest.* 103: 557-564. Long-term sedation may result in tolerance and may necessitate increases in doses (see, e.g., Mayer et al., 1993, *Anesth Analg.* 76: 33-39; Carrasco et al., 1993, *Chest.* 103: 557-564).

When the compounds are used concomitantly with other medications, hypotension and respiratory depression associated with other medications may occur.

For example, opioids may increase the anesthetic or sedative effects of propofol (Crippen, 1992, supra; Ved et al., 1996, *Anesthesiology* 85: 4-10). When analgesic and anxiolytic medications are administered to patients who are receiving a sedative, lower doses of each drug may be necessary (see, e.g., Riker et al., 1994, *Crit Care Med.* 22: 433-440; Olsson et al., 1989, *Heart Lung.* 18: 130-138).

Administration of the compounds by an inhaler is a preferred method of delivery. However, fluorine-substituted alkyl phenols also can be administered orally, intravenously, or intramuscularly as well.

Use As An Anti-Oxidant

The fluorine-substituted alkyl phenols of the invention can be used as anti-oxidants. Oxidants are introduced into an organism through the environment (e.g., upon exposure to sunlight), by smoke inhalation and also are generated during an inflammatory response. When cells are subjected to oxidative stress, cellular functions can be globally affected.

Free radicals produced during oxidative stress can react with proteins, nucleic acids, lipids, and other biological macromolecules producing damage to cells and tissues. Free radicals are atoms, ions, or molecules that contain an unpaired electron (Pryor, 1976, *Free Radicals in Biol.* 1: 1). Free radicals are usually unstable and exhibit short half-lives. Elemental oxygen is highly electronegative and readily accepts single electron transfers from cytochromes and other reduced cellular components. For example, a portion of the $O_2$ consumed by cells engaged in aerobic respiration is univalently reduced to superoxide radical ($O_2^-$) (Cadenas, 1989, *Ann. Rev. Biochem.* 58: 79). Sequential univalent reduction of $O_2^-$ produces hydrogen peroxide ($H_2O_2$), hydroxyl radical, and water.

Free radicals can originate from many sources, including aerobic respiration, cytochrome P-450-catalyzed monooxygenation reactions of drugs and xenobiotics (e.g., trichloromethyl radicals, $CCl_3$., formed from oxidation of carbon tetrachloride), and ionizing radiation. For example, when tissues are exposed to gamma radiation, most of the energy deposited in the cells is absorbed by water and results in scission of the oxygen-hydrogen covalent bonds in water, leaving a single electron on hydrogen and one on oxygen creating two radicals H and OH. The hydroxyl radical is the most reactive radical known in chemistry. It reacts with biomolecules and sets off chain reactions and can interact with the purine or pyrimidine bases of nucleic acids. Radiation-induced carcinogenesis may be initiated by free radical damage (Breimer, 1988, *Brit. J. Cancer* 57: 6). The "oxidative burst" of activated neutrophils produces abundant superoxide radicals, which re believed to be an essential factor in producing the cytotoxic effect of activated neutrophils. Reperfusion of ischemic tissues also produces large concentrations of free oxygen radical, typically superoxide (Gutteridge et al., 1990, *Arch. Biochem. Biophys.* 283: 223). Moreover, superoxide may be produced physiologically by endothelial cells for reaction with nitric oxide, a physiological regulator, forming peroxynitrite, which may decay and give rise to hydroxyl radical (Marletta, 1989, *Trends Biochem. Sci.* 14: 488; Moncada et al., 1989, *Biochem. Pharmacol.* 38: 1709; Saran et al., 1990, *Free Rad. Res. Commun.* 10: 221; Beckman et al., 1990, *Proc. Natl. Acad. Sci. USA*

87: 1620). Additional sources of free oxygen radicals derive from "leakage" of electrons from disrupted mitochondrial or endoplasmic reticular electron transport chains, prostaglandin synthesis, oxidation of catecholamines, and platelet activation.

Oxygen, though essential for aerobic metabolism, can be converted to poisonous metabolites, such as the superoxide anion and hydrogen peroxide, collectively known as reactive oxygen species (ROS). Increased ROS formation under pathological conditions is believed to cause cellular damage through the action of these highly reactive molecules on proteins, lipids, and DNA. During inflammation, ROS are generated by activated phagocytic leukocytes; for example, during the neutrophil "respiratory burst", superoxide anion is generated by the membrane-bound NADPH oxidase. ROS are also believed to accumulate when tissues are subjected to ischemia followed by reperfusion.

Many free radical reactions are highly damaging to cellular components; they crosslink proteins, mutagenize DNA, and peroxidize lipids. Once formed, free radicals can interact to produce other free radicals and non-radical oxidants such as singlet oxygen and peroxides. Degradation of some of the products of free radical reactions can also generate potentially damaging chemical species. For example, malondialdehyde is a reaction product of peroxidized lipids that reacts with virtually any amine-containing molecule. Oxygen free radicals also cause oxidative modification of proteins (Stadtman, 1992, *Science* 257: 1220).

A pharmaceutically effective amount of the compounds described herein can be used prophylactically or in treatment regimens for inhibition of oxidation in subjects that are at risk for developing a disease related to oxidative stress, such as cancer. Further, many neurodegenerative diseases such as Alzheimer's disease, Huntington's disease, Pick disease, multiple sclerosis, and others are associated with oxidative stress. Additional free radical-associated diseases include, but are not limited to: ischemic reperfusion injury, inflammatory diseases (discussed further below), systemic lupus erythematosis, myocardial infarction, stroke, traumatic hemorrhage, spinal cord trauma, cataract formation, uveitis, emphysema, gastric ulcers, oxygen toxicity, neoplasia, undesired cell apoptosis, and radiation sickness (see, e.g., U.S. Pat No. 5,827,880).

A pharmaceutically effective amount for anti-oxidant activity ranges from about 100 mg to 1 g of the compound.

Initial doses of fluorine-substituted alkyl phenols can be determined by a variety of in vitro and in vivo assays. For example, compounds can be tested for their ability to quench free oxygen radicals generated by photo-illumination of riboflavin (see, e.g., Kubow, 1992, *Free Radical Biology and Medicine* 12: 63-81; Frankel, 1984; *JAOCS* 61: 1908-1917; U.S. Pat. No. 6,132,711) or by determining the formation of malondialdehyde degradation products of arachidonic acid after exposure of arachidonic acid to light (see, e.g., U.S. Pat. No. 5,912,179). Electron spin resonance spectroscopy also can be used to verify the formation of phenoxyl radicals of fluorine-substituted alkyl phenols in the presence of free radicals.

Cell-based assays also can be used. In one aspect, a fluorine-substituted alkyl phenol of the invention has anti-oxidant activity if the compound, when added to a cell culture or assay reaction (a "test reaction") produces a detectable decrease in the amount of a free radical, such as superoxide, or a non-radical reactive oxygen species, such as hydrogen peroxide, as compared to a parallel cell culture or assay reaction that is not treated with the compound ("control reactions"). As used herein, a "detectable decrease" is one which is significantly different from the amount of free radical concentrations observed in control reactions using routine statistical tests known in the art and setting p values to <0.05. In one aspect, a detectable decrease is an at least 10% decrease in the amount of a free radical in a test reaction compared to a control reaction, and preferably, a 20%, 30%, 40%, or 50% or greater, reduction.

Suitable concentrations (i.e., an effective dose) in vivo can be determined by various methods, including generating an empirical dose-response curve, predicting potency and efficacy and through other methods used in the pharmaceutical sciences. Since oxidative damage is generally cumulative, there is no minimum threshold level (or dose) with respect to efficacy, although minimum doses for producing a detectable therapeutic or prophylactic effect for particular disease states can be established, as described further below.

Treatment of Disorders Associated With Accumulation of Free Radicals

As discussed above, the inflammatory response that occurs in mammals involves an oxidative component. Thus, the fluorine-substituted alkyl phenols of this invention are useful as anti-inflammatory agents.

In general, the inflammatory response of mammals is dependent on a variety of inflammatory mediators. Many of these mediators, for example, cytokines, TNF-alpha and IL-2, and the eicosanoids, prostacyclins, thromboxanes and leukiotrienes require an oxidation reaction for their production. A pharmacologically effective amount of fluorine-substituted alkyl phenol would inhibit production of these inflammatory mediators and can be administered to subjects where an anti-inflammatory effect is desired. Some examples of inflammatory disorders which can be treated using compounds according to the invention, include, but are not limited to: arthritis, inflammation caused by respiratory diseases or environmental factors, inflammation due to trauma (including complications from surgery), and inflammation caused by disorders of the central nervous system.

Examples of respiratory disorders that can be treated with the fluorinated alkyl phenol compounds include, cystic fibrosis, emphysema, HIV-associated lung disease, chronic obstructive pulmonary disease, asthma, bronchiolitis, bronchopulmonary dysplasia, lung cancer, respiratory distress syndrome (ARD), acid aspiration, idiopathic pulmonary fibrosis, immune-complex-mediated lung injury, ischemia-reperfusion injury, mineral dust pneumoconiosis, Silo-Fillers disease, and others. The preferred method for treatment of these disorders is through the administration of volatile fluorinated alkyl phenol compound to the respiratory tract by using an inhalation device.

A pharmaceutically effective amount of compound delivered as an inhalant ranges from about 0.1 mg to 10 mg per inhalation, several times daily. An oral dose would range from about 1 mg to 500 mg.

In vitro and/or in vivo assays may be used to optimize compounds according to the invention. For example, a bead embolization model of pulmonary inflammation can be used in which antigens are coupled to Sepharose beads, which are embolized to the lungs of mice via injection into their tail veins. The animals preferably are pre-sensitized to the coupled antigen. The immune system of the mouse then mounts a vigorous immune response to the antigen-coupled bead. Focal inflammatory responses, which can last for several weeks, can be examined by examining lung tissue for the size of an embolus and for cytokine production. Hilar lymph nodes and spleens also can be examined. In one aspect, the efficacy of a fluorine-substituted alkyl phenol is determined by monitoring decreases in focal inflammatory responses. Preferably, a therapeutically effective compound is one which decreases a focal inflammatory response as measured by the size of an embolus by at least 30% and which decreases the production of inflammatory cytokines by at least 10%, preferably, at least 20%, at least 30%, at least 40%, and at least 50%.

Other inflammatory disorders which can be treated include, but are not limited to, an autoimmune disease, inflammatory bowel disease, Crohn's disease, ulcerative colitis, a disease caused by an infection of a gram negative bacteria, a degenerative joint disease, such as osteoarthritis, rheumatoid arthritis, rheumatoid spondylitis, or gouty arthritis, asthma (including status asthmaticus), endotoxemia, sepsis, or septic shock.

The fluorine-substituted alkyl phenol compounds of this invention also are useful in treatment of inflammation in the CNS. Inflammation in the CNS can be caused by oxidative stress, viral disease (i.e. meningitis, HIV-1 infection, HIV-II infection), and by traumatic events. Some traumas that can be treated with the compounds described herein include, but are not limited to, concussions, brain hemorrhage, edema, stroke, spinal cord injury, and hematomas.

The antioxidant properties of the fluorine-substituted alkyl phenol compounds described herein also can be exploited in regimens for treatment of cancer. Administration of anti-oxidants during chemotherapy has been found to aid in the inhibition of tumor growth (Chinery et al., 1997, *Nature Medicine* 3: 1233-1241). In addition, many chemotherapeutic agents have a side effect of promoting free radical formation and thus the general anti-oxidant activities of alkyl phenols are beneficial. In a preferred aspect, volatile fluorine-substituted compounds of this invention are particularly useful for treatment of cancers of the respiratory tract. Pharmaceutically effective amounts of compound used in a chemotherapy regime range from about 1 mg to about 500 g of compound delivered daily.

The fluorine-substituted alkyl phenols of this invention also are useful as anti-emetics, which are anti-nauseants. A pharmaceutically effective dose to inhibit nausea and vomiting ranges from about 1 mg to about 500 mg.

The fluorine-substituted phenols of this invention are also useful in the treatment of seizures such as, epileptic seizures. Pharmaceutically effective anti-convulsive dosages range from about 1 mg to about 500 g daily.

In one aspect, fluorine-substituted alkyl phenol compounds are assayed for their ability to scavenge oxygen radicals and cause other beneficial effects on cultured cells, which model inflammatory responses. The anti-inflammatory activity of compounds also may be evaluated in vivo, for example, in animal models (see, e.g., as described in Young et al., 1984, *J. Invest. Dermatol.*, 82: 367-371; U.S. Pat. No. 6,180,796; U.S. Pat. No. 6,177,610; U.S. Pat. No. 6,114,382; and U.S. Pat. No. 6,174,901). Animal models for inflammatory bowel disease include the TNBS colitis model described in Neurath et al., 1995, *J. of Exp. Med.* 182: 1281; IL-2 mutant mice (e.g., Ludviksson et al., 1997, *J. of Immunol.* 158: 104); IL-10 mutant mice (Berg et al., 1996, *J. of Clin. Investigation* 98: 1010); TCR transgenic mice (Mombaerts et al., 1993, *Cell* 75: 274); and SCID mice comprising CD45+ T cells (Powrie et al., 1994, *Immunity* 1: 553). Rheumatoid arthritis models include the murine pristane-induced arthritis model (Stasluk et al., 1997, *Immunol.* 90: 81) and the murine collagen-induced arthritis model (Horsfall et al., 1997, *J. of Immunol.* 159: 5687). Insulin-dependent diabetes (type 1), an autoimmune disease, can be mimicked by NOD mice (Cameron et al., 1997, *J. of Immunol.* 159: 4686). Lupus can be mimicked by an (NZWXNZB) $F_1$ mouse model (Santiago et al., 1997, J. of Exp. Med. 185: 65) and by a GRD, LPR mouse (FAS mutation) (Bhandoola et al., 1994, *Int. Rev. of Immunol.* 11: 231). Multiple sclerosis can be mimicked by mouse models of experimental allergic encephalomyelitis (Karrussis et al., 2001, *J. Neuroimmunol.* 120 (1-2): 1-9. Other animal models are known in the art and are encompassed within the scope of the invention.

In one aspect, the efficacy of a particular dose or type of compound is evaluated by monitoring cytokine production in an animal model of inflammatory disease (e.g., as described above). Splenocytes, lymph nodes and/or intestinal inflammatory cells obtained from treated animals and control animals (e.g., animals receiving carrier but no fluorine-substituted alkyl phenol) can be contacted with antibodies specific for one or more cytokines and reactivity of these cells with inflammatory cytokines can be used to monitor reduction in inflammation. Cells can be analyzed by flow cytometry, by ELISAs, by ELISPOT assays, or by other methods routine in the art. Standard curves can be generated using purified cytokines. Data can be analyzed by routine statistical methods, e.g., such as the one sample t-test, to determine whether mean values significantly differ from zero. Paired t-tests can be used to analyze differences between group means while analysis of variance and/or a Dunnett's t-test can used to analyze multiple comparison data.

Preferably, various clinical parameters of disease are also monitored. For example, in mice, clinical evidence of disease includes weight loss, diarrhea, rectal prolapse and histological evidence of intestinal inflammation. Thus, improvement in these parameters would signify amelioration of disease. To grade intestinal inflammation in animal models, tissue is removed, sectioned and examined histologically, for example, after staining with hematoxylin and eosin. The degree of colonic inflammation can be graded semiquantitatively from 0 to 4 in a blinded fashion by a single pathologist using our usual standardized technique: 0=no inflammation; 1=low level inflammation; 2=intermediate level inflammation; 3=high level inflammation with wall thickening; and 4=transmural infiltration, and loss of goblet cells with wall thickening. Mast cells also can be scanned and counted. Preferably, samples are evaluated blindly.

For mice with collagen-induced arthritis, mice treated with various doses/types of compounds and control mice are examined every other day and their paws scored as follows: 0, normal; 1, Erythema and mild swelling confined to the ankle joint or toes; 2. Erythema and mild swelling extending from the ankle to the midfoot; 3, Erythema and severe swelling extending from the ankle to the metatarsal joints; and 4, Ankylosing deformation with joint swelling. These parameters can be correlated with the histological changes in the arthritic joints. Treatment success results in a decrease in the arthritis score with improvement in the histology. For pristane-induced arthritis, joints may be measured with a micrometer to detect swelling.

Experimental autoimmune encephalomyelitis can be induced in susceptible mice by repeated injection of appropriate sensitizing myelin antigens. In one aspect, mice treated with varying doses of compounds according to the invention and control mice are assessed clinically according to the following criteria: absence of disease; tail atony; hind-limb weakness; hind-limb paralysis; hind-limb paralysis and fore-limb paralysis or weakness; and morbidity. For histological analysis, the spinal cords and brains can be removed and examined histologically (e.g., by fixing the tissues formalin, staining paraffin-embedded sections and examining these using a light microscope. Dispersed splenocytes and cells from other regions can be studied in-vitro as discussed above.

Optimal dosage and modes of administration to subjects in need of treatment can readily be determined by conventional protocols, identifying therapeutic endpoints and identifying minimal doses and routes of administration which achieve these endpoints with minimal adverse effects. For, example in the case of arthritis, therapeutic endpoints may include increased mobility, decrease joint swelling, decreased pain, a reduction in inflammatory cytokines, and the like. Additionally, synovial fluid may be analyzed for cytokine and inflammatory protein concentrations, and for leukocyte composition and function, according to methods known in the art. Synovial biopsies can be performed to provide tissue for histological analysis according to methods known in the art.

In the case of inflammatory bowel disease, such as Crohn's disease, a therapeutic endpoint may include a decrease in the number of exacerbations or an increase in the amount of time between exacerbations of the disease, or a decrease in diarrhea observed over the treatment period. One particularly useful index for the assessment of Crohn's disease is the Crohn's Disease Activity Index, or CDAI (Best et al., 1976, *Gastroenterology* 70: 439). The CDAI incorporates 8 variables related to the disease activity and has been used in most recent studies of therapeutic agents in Crohn's disease. It includes the number of liquid or very soft stools, the severity of abdominal pain or cramping, general well-being, the presence of extraintestinal manifestations of the disease, presence or absence of an abdominal mass, use of antidiarrheal drugs, hematocrit, and body weight. The composite score ranges from 0 to about 600. Scores below 150 indicate remission and scores above 450 indicate severe illness. A tested, accepted and disease specific quality of life questionnaire also may be administered prior to and after treatment to assess therapeutic progress.

The Irvine Inflammatory Bowel Disease Questionnaire is a 32-item questionnaire. It evaluates quality of life with respect to bowel function (e.g. loose stools and abdominal pain), systemic symptoms (fatigue and altered sleep pattern), social function (work attendance and the need to cancel social events) and emotional status (angry, depressed, or irritable). The score ranges from 32 to 224, with higher scores indicating a better quality of life. Patients in remission usually score between 170 and 190. Also, helpful are endoscopic, x-ray and histological assessment of intestinal disease activity. C-reactive protein levels and blood cell sedimentation rate may also be monitored as systemic indicators of inflammation.

In the case of endotoxemia, a decrease in TNF may be monitored, as well as the patient's clinical presentation (e.g., resolution of fever). In the case of asthma, FEV (forced expiratory volume) may be measured as well as signs and symptoms of exacerbation. In humans, MS disease activity is gauged by monitoring progression and remittence of neurological signs and symptoms. The most widely used outcomes measurement is called The Expanded Disability Status Scale. Cerebral spinal fluid protein composition and cell content analyzed according to methods known in the art also may be used to monitor disease activity. Moreover, serial MRI studies show new gadolinium-enhanced brain lesions.

In treatments of respiratory diseases, pulmonary function tests can be used to evaluate lung compliance and function. Inflammatory cells can be obtained from bronchiolar lavages and studied for composition and function. Periodic chest x-ray or CT scans also can help assess disease activity.

Where compounds are used prophylactically, the absence of the appearance of symptoms or a reduction in the severity of symptoms (either overt physical symptoms or measurable biochemical symptoms) may be monitored. It should be obvious to those of skill in the art that the type of therapeutic endpoint will vary with the inflammatory condition being treated and that such endpoints are routinely assayed by those of skill in the art (e.g., physicians and other healthcare workers).

In one embodiment, a therapeutically effective dose of a compound is provided which is a dose effective to reduce by at least about 15%, at least about 50%, or at least about 90% of the expression of a marker associated with disease (e.g., such as pain, lack of mobility, fever, the number of disease episodes, diarrhea, reduction of skin lesions, asthmatic exacerbations, inflammatory cytokines, such as TNF-$\alpha$, TNF-$\beta$, IL-1, IL-6, IL-8, IL-10, IL-13, INF-$\gamma$, and the like).

EXAMPLES

The invention will now be further illustrated with reference to the following examples. It will be appreciated that what follows is by way of example only and that modifications to detail may be made while still falling within the scope of the invention.

Example 1

Synthesis of 6-trifluoromethyl-2-sec-butylphenol 2-sec-Butylphenol (also known as ortho-sec-butylphenol) was reacted with 15% excess sodium iodide (NaI) in the presence of 1,3,4,6-tetrachloro-3$\alpha$,6$\alpha$, -di-phenylglycouril according to the method of Vakkuri et al. 1984 (Vakkuri O, Leppalouto J, Vuolteenaho, O. Acta Endocrinologica, 106: 152-157, 1984). The iodinated phenol products were extracted with chloroform, the chloroform phase reduced under nitrogen, and fractions purified by silica gel column chromatography using ethyl acetate as solvent. Fractions were collected and concentrated under a stream of nitrogen. Products were diluted in ethyl acetate. Mass spectral analyses of the products were determined by GC/MS (gas chromatography/mass spectrometry). The products were determined to be predominantly monoiodo-sec-butylphenols. Each fraction was subjected to proton NMR and determined to be 4-, 5-, and 6-iodo-2-sec-butylphenol. Yields ranged from 5 to 30% of each structural isomer.

6-Iodo-2-sec-butylphenol was isolated and dissolved in dried dimethylformamide (DMF) in a glass flask fitted with a chilled water condenser. CuI and methyl 2,2-difluoro-2-(fluorosulfonyl)acetate are added and the reaction mixture heated to 60-80° C. while stirring with a magnetic stirrer (Chen Q-Y, Wu S-W. J Chem Soc, Chem. Comm, 705-706, 1989). The reaction mixture was maintained at 50-80° C. and the reaction allowed to proceed for up to 3 hr.

The product was passed through a silica gel column using ethyl acetate as mobile phase. A fraction was identified as 2-sec-butyl-6-trifluoromethylphenol by GC/MS.

4-Trifluoromethyl-2-sec-butylphenol and 5-trifluoromethyl-2-sec-butylphenol are made by the same methodology described above, using 4-iodo-2-sec-butylphenol and 5-iodo-2-sec-butylphenol, respectively.

Additionally, 6-bromo-2-sec-butylphenol, 5-bromo-2-sec-butylphenol and 4-bromo-sec-butylphenol can be used to synthesize 4-trifluoromethyl-2-sec-butylphenol, 5-trifluoromethyl-2-sec-butylphenol and 6-trimethyl-2-sec-butylphenol by the method described above (Chen Q-Y, Wu S-W. J Chem Soc, Chem. Comm, 705-706, 1989). 6-, 5- and 4-bromo-2-sec-butylphenol was synthesized by placing 2-sec-butylphenol in a glass reaction flask fitted with a chilled water cooled condenser. Elemental bromine ($Br_2$) was added stepwise until a 15%, and the mixture warmed with stirring with a magnetic stirrer. The reaction was performed for up to 3 hours. Following the reaction, elemental bromine was removed by passing a stream of nitrogen into the reaction flask and stirring. The reaction mixture containing the brominated phenols was chromatographed on a silica gel column using ethyl acetate as mobile phase. The fractions isolated were reduced under a stream of nitrogen and analyzed by GC/MS. 4-, 5-, and 6-bromo-2-sec-butylphenol were identified as products as determined by GC/MS and NMR analysis.

Example 2

6-Trifluoromethyl-2-isopropylphenol Synthesis

2-Isopropylphenol (also known as ortho-isopropylphenol) was reacted with 15% excess sodium iodide (NaI) in the presence of 1,3,4,6-tetrachloro-3α,6α, -di-phenylglycouril as described in Example 1. The iodinated phenol products were extracted with chloroform. The chloroform phase was reduced under nitrogen and fractions purified by silica gel column chromatography using ethyl acetate as solvent. Fractions were collected and dried under nitrogen. Products were dissolved in ethyl acetate and mass spectra (EI) determined by GC/MS. The products were determined to be monoiodo-2-isopropylphenols. Each fraction was subjected to NMR and determined to be 4-, 5-, and 6-iodo-2-isopropylphenols. Yields ranged from 6 to 45% of each structural isomer.

6-Iodo-2-isopropylphenol was dissolved in dried dimethylformamide (DMF) in a glass flask fitted with a chilled water condenser. CuI and methyl 2,2-difluoro-2-(fluorosulfonyl)acetate are added and the reaction mixture heated to 50-80° C. while stirring with a magnetic stirrer. The reaction mixture was maintained at 60-70° C. and the reaction allowed to proceed for up to 2 hr.

The product was passed through a silica gel column using ethyl acetate as mobile phase. A fraction was identified as 2-isopropyl-6-trifluoromethylphenol by GC/MS.

Alternately, 4-trifluoromethyl-2-isopropylphenol and 5-trifluoromethyl-2-isopropylphenol are made by the same methodology described above.

Additionally, 6-bromo-2-isopropylphenol, 5-bromo-2-isopropylphenol and 4-bromo-2-isopropylphenol, made by the reaction of elemental bromine ($Br_2$) with 2-sec-butylphenol (Example 2), can be used to synthesize 4-trifluoromethyl-2-isopropylphenol, 5-trifluoromethyl-2-isopropylphenol and 6-trimethyl-isopropylphenol by the method described above (Chen Q-Y, Wu S-W. J Chem Soc, Chem. Comm, 705-706, 1989.).

Example 3

6-Pentafluoroethyl-2-isopropylphenol Synthesis

6-Bromo-2-isopropylphenol, made as described in Example 2, was reacted with $CF_3CF_2COONa$ in the presence of CuI (Freskos J N, Synth Comm 18:965-972, 1988). This reaction resulted in the synthesis of 6-pentafluoroethyl-2-isopropylphenol.

5-pentafluoroethyl-2-isopropylphenol and 4-pentafluoroethyl-2-isopropylphenol are made as described above using 5-bromo-2-isopropylphenol and 4-bromo-2-isopropylphenol, respectively, as starting compound.

6-pentafluoroethyl-2-sec-butylphenol, 5-pentafluoroethyl-2-sec-butylphenol and 4-pentafluoroethyl-2-sec-butylphenol are made as described above using 6-bromo-2-sec-butylphenol, 5-bromo-2-sec-butylphenol and 4-bromo-2-sec-butylphenol, as synthesized in Example 2, as starting compound.

Example 4

6-Heptafluoro-n-propyl-2-isopropylphenol Synthesis

6-Iodo-2-isopropylphenol, made as described in Example 2, is dissolved in N-methylpyrrolidone (NMP) and reacted with sodium heptafluorobutyrate in the presence of copper iodide (CuI) (Carr G E, Chambers R D, Holmes T F, J. Chem Soc, Perkin I, 921-926, 1988). The reaction was performed at from 50 to 200° C. in a glass flask fitted with a reflux condenser for up to 2 hours. The products were concentrated under vacuum distillation and purifed by silica gel column chromatography. A fraction was identified as 6-heptafluoro-2-isopropylphenol by gas chromatography/mass spectrometry and proton NMR analysis.

6-Heptafluoro-n-propyl-2-sec-butylphenol is made as described above using 6-iodo-2-sec-butylphenol as starting compound.

Variations, modifications, and other implementations of what is described herein will occur to those of ordinary skill in the art without departing from the spirit and scope of the invention.

All of the references identified herein above, are hereby expressly incorporated herein by reference to the extent that they describe, set forth, provide a basis for or enable compositions and/or methods which may be important to the practice of one or more embodiments of the present inventions.

What is claimed is:

1. A compound having the formula:

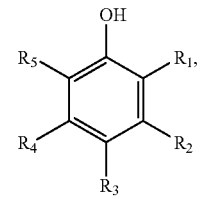

wherein:
$R_1$ is $CH(CH_3)$;
$R_2$ is H;
$R_3$ is H;
$R_4$ is H; and
$R_5$ is $CF_2CF_3$ or $CF_2CF_2CF_3$.

2. The compound of claim 1, wherein $R_5$ is $CF_2CF_3$.

3. The compound of claim 1, wherein $R_5$ is $CF_2CF_2CF_3$.

4. The compound of claim 1, wherein the compound is volatile.

5. The compound of claim 2, wherein the compound is volatile.

6. A pharmaceutical composition comprising the compound of claim 1 and a pharmaceutically acceptable carrier.

7. A pharmaceutical composition comprising the compound of claim 2 and a pharmaceutically acceptable carrier.

8. A compound having the formula:

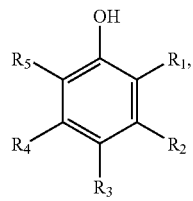

wherein:

$R_1$ is selected from the group consisting of $CH(CH_3)_2$ and $CH(CH_3)CH_2CH_3$;

$R_2$ and $R_4$ are each H;

$R_3$ is selected from F, $CH_3$, and $CF_3$; and $R_5$ is selected from the group consisting of $CF_3$, $CF_2CF_3$ and $CF_2CF_2CF_3$.

9. The compound of claim 8, wherein the compound is volatile.

10. A pharmaceutical composition comprising the compound of claim 8 and a pharmaceutically acceptable carrier.

* * * * *